US011492589B2

(12) United States Patent
Kim et al.

(10) Patent No.: US 11,492,589 B2
(45) Date of Patent: *Nov. 8, 2022

(54) LACTOBACILLUS PLANTARUM CJLP475 STRAIN HAVING ANTIVIRAL AND IMMUNOMODULATORY EFFECTS AND COMPOSITION COMPRISING THE SAME

(71) Applicant: CJ CHEILJEDANG CORPORATION, Seoul (KR)

(72) Inventors: Min-Jeong Kim, Seoul (KR); Hee-Yeon Kim, Seoul (KR); Ho Jin Moon, Seoul (KR); Seo Hyung Woo, Seoul (KR); Kyung Min Lee, Seoul (KR); Yoon Tack Jang, Seoul (KR); Bong Joon Kim, Seoul (KR); Sung Hun Kim, Seoul (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/618,745

(22) PCT Filed: Jul. 12, 2019

(86) PCT No.: PCT/KR2019/008676
§ 371 (c)(1),
(2) Date: Dec. 2, 2019

(87) PCT Pub. No.: WO2020/013669
PCT Pub. Date: Jan. 16, 2020

(65) Prior Publication Data
US 2021/0332323 A1    Oct. 28, 2021

(30) Foreign Application Priority Data

Jul. 13, 2018 (KR) ........................ 10-2018-0081845

(51) Int. Cl.
*A61K 35/747* (2015.01)
*A61K 35/00* (2006.01)
*C12N 1/20* (2006.01)
*A23L 33/135* (2016.01)
*A61K 8/99* (2017.01)
*A23K 10/18* (2016.01)
*A23L 33/00* (2016.01)
*A61P 37/04* (2006.01)
*A61P 31/12* (2006.01)
*C12R 1/25* (2006.01)

(52) U.S. Cl.
CPC .............. *C12N 1/205* (2021.05); *A23K 10/18* (2016.05); *A23L 33/135* (2016.08); *A23L 33/40* (2016.08); *A61K 8/99* (2013.01); *A61K 35/747* (2013.01); *A61P 31/12* (2018.01); *A61P 37/04* (2018.01); *A23V 2002/00* (2013.01); *A23Y 2220/67* (2013.01); *A61K 2035/115* (2013.01); *C12R 2001/25* (2021.05)

(58) Field of Classification Search
None
See application file for complete search history.

(56) References Cited

U.S. PATENT DOCUMENTS

| 9,572,845 | B2 | 2/2017 | Kim et al. |
| 9,572,846 | B2 | 2/2017 | Kim et al. |
| 10,093,995 | B2 | 10/2018 | Kim et al. |
| 10,130,666 | B2 | 11/2018 | Kim et al. |
| 2011/0020395 | A1 | 1/2011 | Benyacoub et al. |

FOREIGN PATENT DOCUMENTS

| CN | 108102959 A | 6/2018 |
| KR | 2003-0063961 A | 7/2003 |
| KR | 10-2010-0063503 | 6/2010 |
| KR | 10-2011-0000854 A | 1/2011 |
| KR | 10-2011-0046020 | 5/2011 |
| KR | 2012-0064416 A | 6/2012 |
| KR | 10-2012-0111608 A | 10/2012 |
| KR | 101235561 B1 * | 3/2013 |
| KR | 10-2013-0056264 | 5/2013 |
| KR | 10-2015-0044764 | 4/2015 |
| KR | 10-2017-0009458 A | 1/2017 |
| KR | 10-2017-0072825 | 6/2017 |
| KR | 10-2019-0063795 A | 6/2019 |

OTHER PUBLICATIONS

Glycerin, p. 1, 2022.*
Teller R. Natural Food Sources of Glucose—Our body's Key Source of Energy, pp. 1-3, 2011.*
English version of KR 101235561 B1, pp. 1-13, 2013.*
U.S. Appl. No. 16/619,050, filed Dec. 3, 2019, Composition Comprising Lactobacillus Plantarum CJLP475 Strain and Lactobacillus Plantarum CJLP17 Strain and Use Thereof.
U.S. Appl. No. 16/619,804, filed Dec. 5, 2019, Composition Comprising Lactobacillus Plantarum CJLP475 Strain and Lactobacillus Plantarum CJLP17 Strain and Use Thereof.
Boricha et al., "In vitro evaluation of probiotic properties of *Lactobacillus* species of food and human origin," *LWT—Food Science and Technology* 106:201-208 (2019).
Pensaert et al., "A New Coronavirus-Like Particle Associated With Diarrhea in Swine," Archives of Virology 58:243-247 (1978).
Shintawati et al., "Lactobacillus plantarum modulatory Effect on the Secretion of Interleukin-10,TGFB, and Fibronectin in Macrophages and Skin Dermal Fibroblasts Culture," International Journal of Science and Research (IJSR) ISSN (Online):2319-7064 Index Copernicus Value (2015):78.96 | Impact Factor (2015):6.391 (6 pages).

(Continued)

Primary Examiner — Sarvamangala Devi
(74) Attorney, Agent, or Firm — Seed IP Law Group LLP (57) ABSTRACT

The present disclosure relates to a novel *Lactobacillus plantarum* CJLP475 strain having acid-resistance, bile-resistance and an immune-enhancing activity, and a composition including the same.

6 Claims, 4 Drawing Sheets
Specification includes a Sequence Listing.

(56) References Cited

OTHER PUBLICATIONS

Song et al., "Porcine epidemic diarrhoea virus: a comprehensive review of molecular epidemiology, diagnosis, and vaccines," Virus Genes 44:167-175 (2012).

Lee et al., "The Effect of *Lactobacillus plantarum* CLP-1 on the Swine Viruses," *Korean Society for Biotechnology and Bioengineering Journal* 26:62-68 (2011) (w/English Abstract).

Lee et al., "Differential Cytokine Regulatory Effect of Three *Lactobacillus* Strains Isolated from Fermented Foods," *J. Microbiol. Biotechnol.* 26(9):1517-1526 (2016).

Sirichokchatchawan et al., "Protective Effects of Cell-Free Supernatant and Live Lactic Acid Bacteria Isolated from Thai Pigs Against a Pandemic Strain of Porcine Epidemic Diarrhea Virus," *Probiotics & Antimicro. Prot.* 10:383-390 (2018).

* cited by examiner

IPEC-J2 cells | Virus-inoculated IPEC-J2 cells | Virus-inoculated IPEC-J2 cells after treatment with culture broth containing CJLP475/ immune cells

```
                        SEQUENCE LISTING

<160> NUMBER OF SEQ ID NOS: 3

<210> SEQ ID NO 1
<211> LENGTH: 1520
<212> TYPE: DNA
<213> ORGANISM: Unknown
<220> FEATURE:
<223> OTHER INFORMATION: Lactobacillus plantarum CJLP475

<400> SEQUENCE: 1
ttggggaccc tgctcaggac gaacgctggc ggcgtgccta atacatgcaa gtcgaacgaa      60
ctctggtatt gattggtgct tgcatcatga tttacatttg agtgagtggc gaactggtga     120
gtaacacgtg ggaaacctgc ccagaagcgg gggataacac ctggaaacag atgctaatac     180
cgcataacaa cttggaccgc atggtccgag tttgaaagat ggcttcggct atcacttttg     240
gatggtcccg cggcgtatta gctagatggt ggggtaacgg ctcaccatgg caatgatacg     300
tagccgacct gagagggtaa tcggccacat tgggactgag acacggccca aactcctacg     360
ggaggcagca gtagggaatc ttccacaatg gacgaaagtc tgatggagca acgccgcgtg     420
agtgaagaag ggtttcggct cgtaaaactc tgttgttaaa gaagaacata tctgagagta     480
actgttcagg tattgacggt atttaaccag aaagccacgg ctaactacgt gccagcagcc     540
gcggtaatac gtaggtggca agcgttgtcc ggatttattg ggcgtaaagc gagcgcaggc     600
ggtttcttaa gtctgatgtg aaagccttcg gctcaaccga agaagtgcat cggaaactgg     660
gaaacttgag tgcagaagag gacagtggaa ctccatgtgt agcggtgaaa tgcgtagata     720
tatggaagaa caccagtggc gaaggcggct gtctggtctg taactgacgc tgaggctcga     780
```

```
aagtatgggt agcaaacagg attagatacc ctggtagtcc ataccgtaaa cgatgaatgc    840
taagtgttgg agggtttccg cccttcagtg ctgcagctaa cgcattaagc attccgcctg    900
gggagtacgg ccgcaaggct gaaactcaaa ggaattgacg ggggcccgca caagcggtgg    960
agcatgtggt ttaattcgaa gctacgcgaa gaaccttacc aggtcttgac atactatgca   1020
aatctaagag attagacgtt cccttcgggg acatggatac aggtggtgca tggttgtcgt   1080
cagctcgtgt cgtgagatgt tgggttaagt cccgcaacga gcgcaaccct tattatcagt   1140
tgccagcatt aagttgggca ctctggtgag actgccggtg acaaaccgga ggaaggtggg   1200
gatgacgtca aatcatcatg ccccttatga cctgggctac acacgtgcta caatggatgg   1260
tacaacgagt tgcgaactcg cgagagtaag ctaatctctt aaagccattc tcagttcgga   1320
ttgtaggctg caactcgcct acatgaagtc ggaatcgcta gtaatcgcgg atcagcatgc   1380
cgcggtgaat acgttcccgg gccttgtaca caccgcccgt cacaccatga gagtttgtaa   1440
cacccaaagt cggtggggta accttttagg aaccagccgc ctaaggtggg acagatgatt   1500
agggtgaagt cgtacaaggg                                               1520

<210> SEQ ID NO 2
<211> LENGTH: 20
<212> TYPE: DNA
<213> ORGANISM: Artificial Sequence
<220> FEATURE:
<223> OTHER INFORMATION: Universal Primer 27F

<400> SEQUENCE: 2
agagtttgat cmtggctcag                                                 20

<210> SEQ ID NO 3
<211> LENGTH: 19
<212> TYPE: DNA
<213> ORGANISM: Artificial Sequence
<220> FEATURE:
<223> OTHER INFORMATION: Universal Primer 1492R

<400> SEQUENCE: 3
ggttaccttg ttacgactt                                                  19
```

LACTOBACILLUS PLANTARUM CJLP475 STRAIN HAVING ANTIVIRAL AND IMMUNOMODULATORY EFFECTS AND COMPOSITION COMPRISING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_456 USPC_SEQUENCE_LISTING.txt. The text file is 2.9 KB, was created on Nov. 24, 2019, and is being submitted electronically via EFS-Web.

TECHNICAL FIELD

The present disclosure relates to a *Lactobacillus plantarum* CJLP475 strain having acid-resistance, bile-resistance, and an immune-enhancing activity. More specifically, the present disclosure relates to a composition, feed additive, food, cosmetic, and pharmaceutical including the *Lactobacillus plantarum* CJLP475 strain and a culture thereof.

BACKGROUND ART

In the current livestock industry, livestock are killed due to highly contagious viral diseases, and this often leads to economic damage to farms. In particular, in the swine industry, infectious diseases caused by viruses and germs, such as porcine respiratory disease complex, postweaning multisystemic wasting syndrome, porcine reproductive and respiratory syndrome, porcine epidemic diarrhea, which are the four major chronic wasting diseases, have caused huge economic losses.

Among them, porcine epidemic diarrhea is a porcine digestive disease caused by the infection of porcine epidemic diarrhea virus (PEDV), a member of the corona virus family. The virus proliferates in the villi of the small intestine and large intestine and causes acute enteritis, vomiting, and watery diarrhea in pigs of all ages, especially in piglets. In particular, the damage is severe mainly in winter, from November to April, and it is known that the mortality rate of pre-weaning piglets within 1 week of birth is about 50%, and in severe cases, the mortality rate can reach almost 100% due to extreme dehydration.

The PED virus was first recognized in Europe in 1971, and G1a type PEDV CV777 was further identified and separated in Belgium in 1976. The virus had spread through Europe in 1980s, and the outbreaks have occurred in East Asian countries including China, Korea, Japan, and Taiwan in 1990s. Further, G2b type PEDV, which is more virulent than the G1a type, had first emerged in China in 2010. The new type PEDV has spread to North America (the United State and Canada) and further to Southeast Asia and Europe, causing severe damage. In 2013, the damage was estimated to about 2.2 trillion won due to the loss of productivity in the US swine industry. In Korea, it is reported that an outbreak of PEDV annually occurs in 20% to 40% of pig farms, causing 6% of the total pigs to be killed. It is also reported that the infection rate of the vehicles entering and leaving slaughterhouses reaches about 60% (Korea Rural Economic Institute, Korea Swine Veterinary Association).

Until now, the only way to prevent the G2b type PED virus is by thorough sterilization. Many farms use an artificial infection method or the existing G1a type PEDV vaccine to prevent the damage caused by viral diseases, but there is a limitation in preventing the G2b type PEDV infection. In order to overcome such problems, development of agents for prevention and treatment of PED virus (vaccines, etc.) and treatment (IgY, essential oil, organic acid, probiotics, etc.) is actively carried out. In particular, a method of enhancing immunity using a functional material that stimulates the immune system in vivo while having an antiviral effect has been recently studied.

Immunity is generally divided into innate immunity and adaptive immunity. Innate immunity is a system that instantly defends pathogen infection from the first line, acting directly on invaders (antigens) or inducing adaptive immunity. Adaptive immunity is a more complex and precise system that recognizes and removes invaders, or acts as a memory for the corresponding invaders, thereby providing more permanent immune functions compared to the innate immunity. Dendritic cells (DCs), macrophages, and natural killer cells, which are antigen-presenting cells related to innate immunity, directly serve innate immune functions and possess receptors that assist in activation of various types of T-cells, thereby secreting cytokines. Adaptive immunity is a secondary defense system against antigens that have entered the body, and is a specific immune response carried out by B lymphocytes and T lymphocytes. The immune responses controlled by antigen-activated T cells include a cytotoxic T cell response and a helper T cell response. The dendritic cells, macrophages, and natural killer cells related to the innate immunity also recognize foreign invasive substances and secrete various kinds of cytokines such as IL-12 and IL-4 to thereby induce a response that appropriately changes the immunity of the host animal, and thus may provide the immune defense mechanism in a suitable direction. Naive CD4 T cells, which act as precursors of T cells, are differentiated by key cytokines. For example, if IL-12 (interleukin-12) is present in a high concentration, CD4 T cells promote the differentiation of Th1 (T helper 1) cells, thereby inducing a CTL (cytotoxic T lymphocyte) response that eradicates intracellular pathogens, whereas, if IL-4 (interleukin-4) is present in a high concentration, they induce a response that specifically eradicates extracellular pathogens (antibody secretion of B cells). In addition, the above-enumerated immune cells respond in an appropriate manner to invaders that have entered the body through an elaborate and complex process, by secreting TGF-beta (Transforming growth factor Beta) and IL-10 to suppress excessive immune responses such as an inflammatory reaction, secreting TGF-beta to inhibit excessive immune response and thereby activates regulatory T cells, stimulating the production of antibodies by transforming B cells into plasma cells in response to the secretion of TGF-beta and IL-6 (interleukin-6), or inducing an immune response (Th17) to eradicate false autoimmunity and extracellular pathogens. However, such immune responses sometimes require an additional and appropriate immune enhancer due to imbalanced or poor immune responses.

DISCLOSURE

Technical Problem

The present inventors have completed the present disclosure by isolating and identifying a novel microorganism capable of activating the immune system while exhibiting an inhibitory activity against the above-mentioned virus, and confirming its activity.

Technical Solution

It is one object of the present disclosure to provide a *Lactobacillus plantarum* CJLP475 strain deposited under Accession No. KCCM12287P.

It is another object of the present disclosure to provide a composition including the *Lactobacillus plantarum* CJLP475 strain, a lysate thereof, a culture thereof, a concentrate thereof or a dried form thereof.

It is still another object of the present disclosure to provide a feed or feed additive including the *Lactobacillus plantarum* CJLP475 strain, a lysate thereof, a culture thereof, a concentrate thereof or a dried form thereof.

It is still further another object of the present disclosure to provide a food including the *Lactobacillus plantarum* CJLP475 strain, a lysate thereof, a culture thereof, a concentrate thereof or a dried form thereof.

It is still further another object of the present disclosure to provide a cosmetic including *Lactobacillus plantarum* CJLP475 strain, a lysate thereof, a culture thereof, a concentrate thereof or a dried form thereof.

It is still further another object of the present disclosure to provide a pharmaceutical including the *Lactobacillus plantarum* CJLP475 strain, a lysate thereof, a culture thereof, a concentrate thereof or a dried form thereof.

It is still further another object of the present disclosure to provide a method for enhancing immunity of a subject, including administering the aforementioned strain or the composition to a subject in need.

It is still further another object of the present disclosure to provide a method for preventing or treating a virus-infected disease of a subject, including administering the aforementioned strain or the composition to a subject in need.

It is still further another object of the present disclosure to provide the use of the *Lactobacillus plantarum* CJLP475 strain for prevention or treatment of a virus-infected disease.

Advantageous Effects

The *Lactobacillus plantarum* CJLP475 strain of the present disclosure has high acid-resistance and bile-resistance and can thus be provided as a probiotic. The strain activates immune cells in vivo and thereby regulates immune functions, and particularly exhibits an excellent inhibitory activity against Porcine epidemic diarrhea virus (PEDV) infection. In addition, when the *Lactobacillus plantarum* CJLP475 strain of the present disclosure was orally administered to livestock, it exhibited an immunomodulatory effect. Accordingly, the present disclosure can provide a novel *Lactobacillus plantarum* CJLP475 strain having an antiviral activity against PED virus and an immunity-enhancing activity, and thus, the strain can be effectively used as a feed composition, a food composition, a cosmetic composition or a pharmaceutical composition.

DETAILED DESCRIPTION OF EMBODIMENTS

Hereinafter, the present disclosure will be described in more detail. Meanwhile, each description and embodiment disclosed herein can be applied to other descriptions and embodiments, respectively. That is, all combinations of various elements disclosed herein fall within the scope of the present disclosure. Further, the scope of the present disclosure is not limited by the specific description described below.

One aspect of the present disclosure to overcome the objects above, there is provided a *Lactobacillus plantarum* CJLP475 strain deposited under Accession No. KCCM12287P. The strain is a strain having the biochemical property of the sugar fermentation pattern shown in Table 3 which is represented by 16s rDNA nucleotide sequence of SEQ ID NO: 1, and as a result of 16S r DNA analysis, no same strain was found, and therefore, it is a strain newly identified by the present inventors.

The strain may have acid-resistance, bile-resistance, and an immune-enhancing activity.

As used herein, the term "*Lactobacillus*" is a microorganism of aerobic or facultative anaerobic gram-positive *bacillus* widely distributed in nature. The microorganisms belonging to the genus *Lactobacillus* include Lactobacilus plantarum, etc. The present inventors provide a novel strain belonging to the *Lactobacillus plantarum*, which was deposited under Accession No. KCCM12287P, and is designated as "*Lactobacillus plantarum* CJLP475". This corresponds to a probiotic strain, which is harmless to the human body and can be used without side effects.

As used herein, the term "probiotics" refers to live bacteria that enter the body and provide a healthy benefit. Most of the probiotics known so far have been consumed through fermented milk products made from lactic acid bacteria such as *Lactobacillus*. In recent years, however, probiotics are available on the market in the form of fermented milk, granules, powder and the like, containing some of the bacteria such as *Bifidobacterium* and *Enterococcus*, in addition to *Lactobacillus*. The *Lactobacillus plantarum* CJLP475 of the present disclosure may also be used in the form of fermented milk, granules, powder and the like, but are not limited thereto.

As used herein, the term "acid-resistance" refers to the property of withstanding high acidity. If the probiotics are acid-resistant, they can be prevented from being degraded or damaged even when exposed to strong acidic conditions in the stomach, by consumption through various routes of administration including oral administration.

As used herein, the term "bile-resistance" refers to the resistance to digestive enzymes in the bile. The bile is made from the liver and stored in the gallbladder, and is a weak alkaline greenish brown liquid that helps the digestion of fat in the duodenum of the small intestines. It emulsifies fat to help digestion and absorption. The bile is one of the major causes of reducing the effect of probiotic administration as they act on probiotics ingested through various routes including oral administration and the like.

The *Lactobacillus plantarum* CJLP475 strain of the present disclosure has the acid-resistance and bile-resistance at the same time, and thus can be used as an excellent probiotic.

Specifically, the *Lactobacillus plantarum* CJLP475 strain was obtained by isolating it from soy sauce (i.e., a traditional fermented food). The morphological characteristics of the strain of the present disclosure is that the strain is a gram-positive *bacillus* and is represented by 16s rDNA nucleotide sequence of SEQ ID NO: 1. The nucleotide sequences was analyzed and found to be about 99% homologous with *Lactobacillus plantarum*. Accordingly, the present inventors deposited the novel isolated *Lactobacillus plantarum* CJLP475 strain at the Korean Culture Center of Microorganisms located at Yurim B/D, 45, Hongjenae-2ga-gil, Seodaemun-gu, Seoul 03641, Republic of Korea, an International Depositary Authority, under Budapest Treaty on Jul. 11, 2018, with Accession No. KCCM12287P.

In order to stably maintain the *Lactobacillus plantarum* CJLP475 strain of the present disclosure for a long period of time, the strain may be stored by dissolving the cells in a storage solution prepared by mixing a certain amount of glycerol in water at −70° C., or may be freeze-dried by suspending the cells in sterilized 10% skim milk, but it is not limited thereto, and may be stored for a long time by various known methods.

The *Lactobacillus plantarum* CJLP475 strain of the present disclosure may not exhibit a hemolytic activity against red blood cells. Hemolysis refers to the destruction of red blood cells and the release of hemoglobin to the surrounding area, and is an action by which the red blood cells are hemolyzed by enzymes produced from harmful bacteria in vivo. Therefore, the strain is recognized as a safe microorganism that does not cause hemolysis in the blood vessel even if the CJLP475 is administered in vivo.

In addition, the *Lactobacillus plantarum* CJLP475 strain of the present disclosure may have a weak resistance or no resistance to antibiotics. The antibiotics may specifically be, but are not limited to, ampicillin, clindamycin, gentamicin, kanamycin, erythromycin, ampicillin/sulbactam, chloramphenicol, or streptomycin. Accordingly, even when the CJLP475 is used in pharmaceuticals, health functional foods, feed additives, or the like, it has no resistance to antibiotics, and thus, the possibility of causing relevant pharmacological effects or environmental problems is low.

The *Lactobacillus plantarum* CJLP475 strain may enhance the activation of immune cells to increase secretion of cytokines, or may be administered in vivo to promote immune function.

As used herein, the term "immune cells" refers to all cells that play a role in immune function in vivo, and can be largely divided into T cells and B cells. The immune cells may include, but are not limited to, Th1 or Th2 cells. The *Lactobacillus plantarum* CJLP475 strain of the present disclosure may have an activity to stimulate immune cells and thereby increase the secretion of cytokines such as IL-12, IL-10, or TGF-beta.

In viral diseases, which generally show a high mortality rate, necrosis of cells or tissues themselves due to the virus can lead to a secondary infection and septicemia induced by other bacteria, an inflammatory disease caused by an over-activated immune response, or appetite reduction and dehydration. Therefore, when the antiviral efficacy (related to Th1, Th2), which suppresses the viral infection, and the immune response (Th2, anti-inflammation), which regulates the secondary infection and the excessive inflammation reaction, are simultaneously enhanced, an effective prevention and treatment effect for viral diseases can be achieved. As such, a strain that simultaneously enhances Th1 and Th2 in regards to providing an immune-enhancing effect through probiotics is not known in the art, and such a strain has been newly discovered by the present inventors. In addition, the *Lactobacillus plantarum* CJLP475 strain of the present disclosure has an immunomodulatory ability to regulate the Th1/Th2 imbalance.

As used herein, the term "cytokine" refers to a glycoprotein used as a signal substance for controlling and stimulating a body defense system, and may be, for example, IL-12, IL-10, or TGF-beta, but is not limited thereto.

The strain may have an immune-activating effect upon administration to a subject.

As used herein, the term "subject" may refer to all animals including humans in which the immunity is weakened or likely to be weakened. For example, the subject may include animals excluding humans or including humans. The animal may include not only humans, but also all animals that need the above-mentioned efficacy to be revealed, and may specifically be mammals such as cows, horses, sheep, pigs, goats, camels, antelopes, dogs, cats, and the like, or alternatively, it may be a livestock or pet.

The above administration method is not particularly limited, but may be administered through various routes including an oral or parenteral route as long as it can reach the target tissues. Examples thereof may be an oral administration.

The strain may have an antiviral activity against the porcine epidemic diarrhea virus (PEDV).

As used herein, the term "anti-virus" refers to the property of inhibiting a viral infection. Probiotics cannot inactivate a virus themselves, but can increase the immunity of a virus-infected subject by an immunological activity, thereby allowing to resist the viral infection.

Porcine epidemic diarrhea virus is a coronavirus that infects the cells lining of the small intestine of pigs, causing porcine epidemic diarrhea which induces severe diarrhea and dehydration. The virus may include any virus, whose infection can be inhibited by the *Lactobacillus plantarum* CJLP475 strain of the present disclosure, without limitation.

When the *Lactobacillus plantarum* CJLP475 strain, a lysate thereof, a culture thereof, a concentrate thereof, or a dried form thereof is treated on a subject, the activity and infection of PED virus can be remarkably suppressed. Accordingly, the composition including the *Lactobacillus plantarum* CJLP475 strain, a lysate thereof, a culture thereof, a concentrate thereof, or a dried form thereof may be used as an antiviral composition against a PED virus, or a pharmaceutical, a health functional food composition, a medicinal composition, or a feed composition for preventing or improving porcine epidemic diarrhea.

In another aspect of the present disclosure, there is provided a composition including the *Lactobacillus plantarum* CJLP475 strain, a lysate thereof, a culture thereof, a concentrate thereof, or a dried form thereof. Further details regarding the composition can be made reference to the above description.

The newly isolated strain of the present disclosure can be cultured by a conventional method for culturing *Lactobacillus* strains. As the medium, a natural medium or a synthetic medium can be used. As the carbon source of the medium, for example, glucose, sucrose, dextrin, glycerol, starch and the like may be used. As the nitrogen source, peptone, meat extracts, yeast extracts, dried yeasts, soybean, ammonium salts, nitrate and other organic or inorganic nitrogen-containing compounds may be used, but is not limited thereto. As the inorganic salts included in the medium, magnesium, manganese, calcium, iron, potassium, and the like may be used, but is not limited thereto. Amino acids, vitamins, nucleic acids and relevant compounds may be added to the medium in addition to the carbon source, the nitrogen source, and the components of the inorganic salt. The newly isolated strain of the present disclosure may be cultured for 12 hours to 4 days in a temperature range of 20° C. to 40° C.

Specifically, the culture broth of the newly isolated strain may be a culture broth containing cells, and may also be cells from which a culture supernatant is removed, or a concentration thereof. The composition of the culture broth may additionally contain not only components required for conventional culture of *Lactobacillus*, but also components that act synergistically to the growth of *Lactobacillus*, and the compositions thereof may be readily selected by those skilled in the art.

In addition, the strain may be in a liquid state or a dry state, and the drying method may include, but not limited to, air drying, natural drying, spray drying, and freeze drying.

In the composition, the concentration of the *Lactobacillus plantarum* CJLP475 strain may be, but is not limited to, $10^3$ CFU/mL to $10^{10}$ CFU/mL, $10^3$ CFU/mL to $10^9$ CFU/mL, $10^3$ CFU/mL to $10^8$ CFU/mL, $10^3$ CFU/mL to $10^7$ CFU/mL, $10^3$ CFU/mL to $10^6$ CFU/mL, $10^3$ CFU/mL to $10^5$ CFU/mL, $10^3$ CFU/mL to $10^4$ CFU/mL, $10^4$ CFU/mL to $10^{10}$ CFU/mL, $10^5$ CFU/mL to $10^{10}$ CFU/mL, $10^6$ CFU/mL to $10^{10}$ CFU/mL, $10^7$ CFU/mL to $10^{10}$ CFU/mL, $10^8$ CFU/mL to $10^{10}$ CFU/mL, $10^9$ CFU/mL to $10^{10}$ CFU/mL, $10^4$ CFU/mL to $10^9$ CFU/mL, $10^5$ CFU/mL to $10^8$ CFU/mL, or $10^6$ CFU/mL to $10^7$ CFU/mL.

The composition may further include a cryoprotectant or an excipient. The cryoprotectant or excipient may be a non-naturally occurring substance or a naturally occurring substance, but is not limited thereto. In another embodiment, the cryoprotectant or excipient may be a substance that does not naturally contact with the *Lactobacillus plantarum* CJLP475 strain, or a substance that is not naturally contained simultaneously with the strain, but is not limited thereto. In still another embodiment, the composition may further include at least one cryoprotectant selected from the group consisting of glycerol, trehalose, maltodextrin, skim milk powder, and starch; and/or at least one excipient selected from the group consisting of glucose, dextrin, and skim milk. The cryoprotectant of the present disclosure may be contained in an amount of 0.01% to 20% by weight and 0.01% to 10% by weight based on the total weight of the composition. Specifically, the glycerol may be contained in an amount of 5% to 20% by weight, the trehalose may be contained in an amount of 2% to 10% by weight, the maltodextrin may be contained in an amount of 2% to 10% by weight, the skim milk powder may be contained in an amount of 0.5% to 2% by weight, and the starch may be contained in an amount of 0.1% to 1% by weight in the composition. In addition, the excipient may be contained in an amount of 75% to 95% by weight or 85% to 95% by weight based on the total weight of the composition.

Further, the method for preparing the composition including the *Lactobacillus plantarum* CJLP475, a lysate thereof, a culture thereof, a concentrate thereof, or a dried product thereof may include adding the *Lactobacillus plantarum* CJLP475 strain, a lysate thereof, a culture thereof, a concentrate thereof, or a dried product thereof with an additive. The additive may be the above-mentioned cryoprotectant or excipient.

The composition may be used for enhancing immunity.

The composition may be used for providing an antiviral activity.

The composition may be used for a food, a functional food, a feed, a feed additive, a cosmetic composition, or a pharmaceutical composition.

In still another aspect, there is provided a probiotic composition including the *Lactobacillus plantarum* CJLP475 strain, a lysate thereof, a culture thereof, a concentrate thereof, or a dried product thereof as an active ingredient.

Probiotics are fixed on the walls of the digestive tract in the intestines to prevent the establishment of harmful bacteria and inhibit the proliferation of viruses. In addition, the beneficial digestive enzymes produced by probiotics promote growth by facilitating the absorption and utilization of nutrients.

A method for preparing the probiotic composition may include culturing a *Lactobacillus plantarum* CJLP475 strain deposited under Accession No. KCCM12287P: and mixing the recovered strain with an additive.

In one embodiment, the additive may be a cryoprotectant, and the method may further include a freeze-drying step after the mixing step.

Herein, the bacteria in the freeze-dried composition may be in a live state.

In another embodiment, the preparation method may include preparing a predetermined amount of the composition into a package after the mixing step.

Herein, in the packaging step, the composition may be prepared into a package such that the total amount of strain including the CJLP475 strain is $10^6$ CFU/g or more.

In still further another aspect of the present disclosure, there is provided a feed or a feed additive including the *Lactobacillus plantarum* CJLP475 strain, a lysate thereof, a culture thereof, a concentrate thereof, or a dried product thereof.

The above *Lactobacillus plantarum* CJLP475 strain is as described above. Specifically, the *Lactobacillus plantarum* CJLP475 strain of the present disclosure may be added to a feed additive or a feed including the feed additive for the purpose of promoting growth, reducing diarrhea incidence, and inhibiting viral activity.

As used herein, the term "feed additive" refers to substances added to a feed for the purpose of providing various effects, such as supplementing nutrients and preventing weight loss, promoting digestibility of cellulose in the feed, improving milk quality, preventing reproductive disorders and improving pregnancy rate, and preventing a high-temperature stress during the summer season. The feed additive of the present disclosure belongs to a supplementary feed according to the Control of Livestock and Fish Feed Act and may further include mineral preparations such as sodium hydrogen carbonate, bentonite, magnesium oxide, complex minerals, and trace minerals including zinc, copper, cobalt, and selenium; vitamins such as carotene, vitamin E, vitamins A, D, E, nicotinic acid, and vitamin B complex; amino acid protective agents such as methionine and lysine; fatty acid protective agents such as fatty acid calcium; and live bacteria and yeast preparations such as probiotics (lactic acid bacteria), yeast culture, and fungus fermented product.

As used herein, the term "feed" refers to any natural or artificial diet, a single meal, or the like, or a component of the single meal, which an animal eats, ingests and digests or which is suitable for eating, ingestion and digestion. The feed including the composition for preventing or treating a metabolic disease according to the present disclosure as an active ingredient may be prepared into various forms of feeds known in the art, and may include a concentrated feed, a crude feed and/or a specialty feed.

The subjects to be raised may include any organism that can ingest the feed of the present disclosure, and may include pigs for the purpose of the present disclosure.

The content of the *Lactobacillus plantarum* CJLP475 strain in the feed composition according to the present disclosure may be properly controlled depending on the kind and age of subject to be applied, application forms, desired effects, and the like. For example, the composition may be contained in an amount of 0.01% to 20% by weight, 0.01% to 15% by weight, 0.01% to 10% by weight, 0.01% to 5% by weight, 0.01% to 1% by weight, 1% to 20% by weight, 1% to 15% by weight, 1% to 10% by weight, 1% to 5% by weight, 5% to 20% by weight, 5% to 15% by weight, 5% to 10% by weight, 10% to 20% by weight, 10% to 15% by weight, or 15% to 20% by weight, but is not limited thereto.

For administration, the feed composition of the present disclosure may further include a mixture of one or more of an organic acid such as citric acid, fumaric acid, adipic acid, lactic acid, and the like; phosphate such as potassium phosphate, sodium phosphate, polyphosphate, and the like; and a natural antioxidant such as polyphenol, catechin, tocopherol, vitamin C, green tea extract, chitosan, tannic acid, and the like. If necessary, other typical additives such as an anti-influenza agent, a buffer, a bacteriostatic agent, and the like may be added. Further, a diluent, a dispersing agent, a surfactant, a binder, or a lubricant may be additionally added to formulate the composition into an injectable preparation such as an aqueous solution, a suspension, an emulsion, and the like, a capsule, a granule, or a tablet.

Further, the feed composition of the present disclosure may be used together with a nutrient supplement, a growth accelerator, a digestion-absorption accelerator, and a prophylactic agent, in addition various auxiliaries such as amino acids, inorganic salts, vitamins, antioxidants, antifungal agents, antimicrobial agents, and the like, as auxiliary components, and the main ingredients including vegetable protein feeds such as pulverized or fragmented wheat, barley, corn, and the like, animal protein feeds such as blood meal, meat meal, fish meal, and the like, animal fat and vegetable fat.

When the feed composition of the present disclosure is used as a feed additive, the feed composition may be added as it is or used together with other components, and may be appropriately used according to a conventional method. The feed composition may be prepared in the administration form of an immediate release or a sustained release formulation, in combination with a non-toxic, pharmaceutically acceptable carrier. The carrier may be a non-naturally occurring substance or a naturally occurring substance, but is not limited thereto. In another embodiment, the carrier may be a substance that does not naturally contact with the *Lactobacillus plantarum* CJLP475 strain, or a substance that is not naturally contained simultaneously with the strain, but is not limited thereto. The edible carrier may be corn starch, lactose, sucrose, or propylene glycol. A solid carrier may be in the administration form of tablets, powders, troches, and the like, and a liquid carrier may be in the administration form of syrups, liquid suspensions, emulsions, solutions, and the like. Further, the administration agent may include a preservative, a lubricant, a solution accelerator, or a stabilizer, and may also include other agents for improving inflammatory diseases and substances useful for the prevention of virus.

The feed composition according to the present disclosure may be mixed with a feed in an amount of about 10 g to 500 g, specifically 10 g to 100 g per 1 kg, based on the dry weight of the feed. After being completely mixed, the feed composition may be provided as mash, or may be further subjected to a pelletizing, extensification, or extrusion process, but is not limited thereto.

In still further another aspect of the present disclosure, there is provided a food composition or a functional food including the *Lactobacillus plantarum* CJLP475 strain, a lysate thereof, a culture thereof, a concentrate thereof, or a dried product thereof.

Specifically, the composition of the present disclosure may be added to a food composition for the purpose of promoting growth, reducing diarrhea incidence, promoting immunity, and inhibiting viral activity. The *Lactobacillus plantarum* CJLP475 strain is as described above. The food composition may include a sitologically acceptable carrier. The carrier may be a non-naturally occurring substance or a naturally occurring substance, but is not limited thereto. In another embodiment, the carrier may be a substance that does not naturally contact with the *Lactobacillus plantarum* CJLP475 strain, or a substance that is not naturally contained simultaneously with the strain, but is not limited thereto.

The food composition of the present disclosure includes all forms of functional foods, nutritional supplements, health foods and food additives, and these types of food composition may be prepared into various forms according to conventional methods.

When the *Lactobacillus plantarum* CJLP475 strain is used as a food additive, the *Lactobacillus plantarum* CJLP475 strain may be added either alone or used in combination with other foods or food ingredients, and may be appropriately used according to a conventional method. The amount of mixed active ingredients may appropriately be determined depending on the purpose of use (prevention, health, or therapeutic treatment). In general, at the time of preparing a food or drink, the *Lactobacillus plantarum* CJLP475 strain is added in an amount of 0.0001% to 1% by weight, specifically 0.0001% to 0.1% by weight based on a raw material composition including the *Lactobacillus plantarum* CJLP475 strain. However, in the case of long-term administration for health and hygiene purposes or for the purpose of controlling health, the amount may be less than the above-described range.

There is no particular limitation on the type of the food. Examples of foods to which the composition can be added include meats, sausages, bread, chocolates, candies, snacks, confectionaries, pizzas, instant noodles, other noodles, gums, dairy products including ice creams, various kinds of soup, beverages, teas, drinks, alcoholic drinks, vitamin complexes, and the like, and all health functional foods in the ordinary sense are included.

The health drink composition of the present disclosure may further contain, as additional components, various flavoring agents or natural carbohydrates, as in conventional drinks. The aforementioned natural carbohydrates may include monosaccharides such as glucose, fructose, and the like: disaccharides such as maltose, sucrose, and the like; polysaccharides such as dextrin, cyclodextrin, and the like; and sugar alcohols such as xylitol, sorbitol, erythritol, and the like. Natural sweetening agents such as thaumatin, a *stevia* extract, and the like; and synthetic sweetening agents such as saccharin, aspartame, and the like may be used as the sweetening agent. A ratio of the additional components may be in a range of 0.01 to 0.04 parts by weight, specifically 0.02 to 0.03 parts by weight based on 100 parts by weight of the composition of the present disclosure.

In addition to the aforementioned components, the composition of the present disclosure may contain various nutritional supplements, vitamins, electrolytes, flavoring agents, coloring agents, pectic acid and salts thereof, alginic acid and salts thereof, organic acids, protective colloidal thickening agents, pH control agents, stabilizing agents, preservatives, glycerin, alcohols, carbonating agents used in carbonated drinks and the like. The ratio of such additives is not important, but is generally chosen in a range of 0.01 to 0.1 parts by weight, based on 100 parts by weight of the composition of the present disclosure. Moreover, the composition of the present disclosure may include pulp for preparing a natural fruit juice, a fruit juice drink or a vegetable drink. The ratio of such pulp is not important, but is generally chosen in a range of 0.01 to 10 parts by weight, based on 100 parts by weight of the composition of the present disclosure. Such components may be used alone or in combination.

In still further another aspect of the present disclosure, there is provided a cosmetic including the *Lactobacillus plantarum* CJLP475 strain, a lysate thereof, a culture thereof, a concentrate thereof, or a dried product thereof.

Specifically, the composition of the present disclosure has an anti-inflammatory effect and an antiviral activity-inhibiting effect through immunity stimulation, and thus can be used as a cosmetic. The *Lactobacillus plantarum* CJLP475 strain is as described above.

When the composition according to the present disclosure is used as a cosmetic, the composition may be prepared into various cosmetics in the conventional formulations known in the field of cosmetics. Upon preparation into each formulation, it may be prepared by adding a carrier or an excipient which is acceptable and necessary in the manufacture of the cosmetics for each formulation. The carrier may be a non-naturally occurring substance or a naturally occurring substance, but is not limited thereto. In another embodiment, the carrier may be a substance that does not naturally contact with the *Lactobacillus plantarum* CJLP475 strain, or a substance that is not naturally contained simultaneously with the strain, but is not limited thereto.

In still further another aspect of the present disclosure, there is provided a pharmaceutical including the *Lactobacillus plantarum* CJLP475 strain, a lysate thereof, a culture thereof, a concentrate thereof, or a dried product thereof.

When the composition according to the present disclosure is used as a pharmaceutical, the composition may be prepared into a conventional pharmaceutical formulation known in the art. The pharmaceutical may specifically be prepared into formulations for oral administration such as liquids, suspensions, powder, granules, tablets, capsules, pills, or extracts. Upon preparation into each formulation, it may be prepared by adding a carrier or an excipient which is acceptable and necessary in the manufacture of the cosmetics for each formulation. The carrier may be a non-naturally occurring substance or a naturally occurring substance, but is not limited thereto. In another embodiment, the carrier may be a substance that does not naturally contact with the *Lactobacillus plantarum* CJLP475 strain, or a substance that is not naturally contained simultaneously with the strain, but is not limited thereto. Typically, when the composition is prepared into a formulation for oral administration, at least one carrier selected from a diluent, a lubricant, a binder, a disintegrating agent, a sweetener, a stabilizer, and a preservative may be used, and at least one additive selected from a flavoring agent, a vitamin, and an antioxidant may be used. Any pharmaceutically acceptable excipient or additive may be used. Specifically, it is possible to use lactose, corn starch, soybean oil, microcrystalline cellulose, or mannitol as the diluent; magnesium stearate or talc as the lubricant; and polyvinyl pyrrolidone or hydroxypropyl cellulose as the binder. In addition, it is possible to use calcium carboxymethylcellulose, sodium starch glycolate, polacrilin potassium, or crospovidone as the disintegrating agent; white sugar, fructose, sorbitol, or aspartame as the sweetener; sodium carboxymethylcellulose, (i-cyclodextrin, white wax, or xanthan gum as the stabilizer, and methyl paraoxybenzoate, propyl paraoxybenzoate, or potassium sorbate as the preservative.

In still further another aspect of the present disclosure, there is provided a step of administering the *Lactobacillus plantarum* CJLP475 strain or the composition of the present disclosure to a subject. The *Lactobacillus plantarum* CJLP475 strain, the composition, and the subject are as described above.

The dosage for the administration may be, but is not limited to, $10^6$ CFU/day or more, $10^7$ CFU/day or more, 10 CFU/day or more, $10^9$ CFU/day or more, $10^{10}$ CFU/day or more or $10^{11}$ CFU/day or more based on the *Lactobacillus plantarum* CJLP475 strain.

In still further another aspect of the present disclosure, there is provided a method for enhancing immunity of a subject, including administering the *Lactobacillus plantarum* CJLP475 strain or the composition of the present disclosure to a subject in need. The *Lactobacillus plantarum* CJLP475 strain, the composition, and the subject are as described above.

As used therein, the term "administration" means introducing the strain or the composition of the present disclosure to a subject by any appropriate method, and the administration route may include various routes such as oral or parenteral administration as long as it can reach the target tissue.

In still further another aspect of the present disclosure, there is provided a method for preventing or treating a virus-infected disease of a subject, including administering the *Lactobacillus plantarum* CJLP475 strain or the composition of the present disclosure to a subject in need. The *Lactobacillus plantarum* CJLP475 strain is as described above.

As used herein, the term "prevention" or "preventing" means all actions that are intended to inhibit, suppress, or delay a virus-infected disease by administration of the *Lactobacillus plantarum* CJLP475 strain or the composition of the present disclosure. Further, as used herein, the term "treatment" or "treating" means all actions that are intended to ameliorate or beneficially change a symptom of a virus-infected disease by administration of the *Lactobacillus plantarum* CJLP475 strain or the composition of the present disclosure.

DETAILED DESCRIPTION OF EMBODIMENTS

Hereinafter, the present disclosure will be described in more detail by way of Examples. However, these Examples are given for illustrative purposes only, and the scope of the invention is not intended to be limited by these Examples.

Example 1: Separation and Selection of Strains 1-1. Sample Collection and Separation of Strains The *Lactobacillus plantarum* CJLP475, the subject strain of the present disclosure, is a novel strain of *Lactobacillus planlarum* isolated and identified from soy sauce (i.e., a traditional fermented food). The collected samples were subjected to a serial dilution, smeared on a solid MRS medium and incubated at 37° C. for 24 hours. The strains isolated from each sample were purely isolated by transferring them to a fresh medium, and the thus-isolated strains were stored in a nutrient medium supplemented with 20% glycerol at −70° C. or below. The strains having excellent antiviral activity were selected through the following examples.

1-2. Assessment of Acid-Resistance and Bile-Resistance of Strains

In order to select the strains that can be used as probiotics, acid-resistance and bile-resistance activity of the obtained strains were assessed.

An artificial gastric juice medium was prepared for the assessment of acid-resistance. More specifically, the artificial gastric juice medium was prepared by adding pepsin to a liquid MRS medium so as to adjust the pH to 2.5, followed by sterilization.

The strains of Example 1-1 were subjected to a static culture in a liquid MRS medium at 37° C. for 18 hours after the second subculture, 1% of the pre-incubated strains were inoculated to the artificial gastric juice medium and subjected to a static culture at 37° C., and the culture broth was sampled at 0 hour and 3 hours. The sampled culture broth was serial diluted and smeared on the solid MRS medium, and incubated at 37° C. for 48 hours to measure viable cell count.

An artificial bile medium was prepared for the assessment of bile-resistance. More specifically, the artificial bile medium was prepared by adding 0.5% oxgall(bull bile) to a liquid MRS medium, followed by sterilization.

The strains of Example 1-1 were subjected to a static culture in a liquid MRS medium at 37° C. for 18 hours after the second subculture. 1% of the pre-incubated strains were inoculated to the artificial bile medium and subjected to a static culture at 37° C., and the culture broth was sampled at 0 hour and 24 hours. The sampled culture broth was serial diluted and smeared on the solid MRS medium, and incubated at 37° C. for 48 hours to measure viable cell count.

Through the above assessments, the strain having the highest acid-resistance and bile-resistance were selected and designated as *Lactobacillus plantarum* CJLP475. The selected strains were identified as *Lactobacillus plantarum* as confirmed by the following Examples. In order to compare the acid-resistance and bile-resistance of the CJLP475 strain with those of the conventionally known strains, the acid-resistance and the bile-resistance of the *Lactobacillus plantarum* standard strain (KCCM12116) obtained from the Korean Culture Center of Microorganisms were assessed in the same manner as the above method.

TABLE 1

| Acid-Resistance Assessment (unit: CFU/mL) | | |
| --- | --- | --- |
| | 0 hr | 3 hr |
| *Lactobacillus plantarum* CJLP475 (KCCM12287P) | $4.0 \times 10^6$ | $3.25 \times 10^6$ |
| *Lactobacillus plantarum* (KCCM12116) | $2.3 \times 10^7$ | $1.3 \times 10^7$ |

TABLE 2

| Bile-Resistance Assessment (Unit: CFU/mL) | | |
| --- | --- | --- |
| | 0 hr | 24 hr |
| *Lactobacillus plantarum* CJLP475 (KCCM12287P) | $5.2 \times 10^6$ | $1.7 \times 10^7$ |
| *Lactobacillus plantarum* (KCCM12116) | $2.1 \times 10^7$ | $1.6 \times 10^6$ |

According to the above Tables 1 and 2, the number of cells in the *Lactobacillus plantarum* standard strain (KCCM12116) in the artificial gastric juice medium and the artificial bile medium was decreased. As a result, it can be seen that not all commonly known *Lactobacillus plantarum* have acid-resistance and bile-resistance.

In contrast, the *Lactobacillus plantarum* CJLP475 strain had a smaller decrease in the number of cells as compared with the *Lactobacillus plantarum* standard strain (KCCM12116) in the acid-resistance assessment, and the number of cells was rather increased in the bile-resistance assessment. These results indicate that the *Lactobacillus plantarum* CJLP475 strain has excellent acid-resistance and bile-resistance.

1-3: Investigation of Morphological and Biochemical Characteristics of Strain

Figure 1:
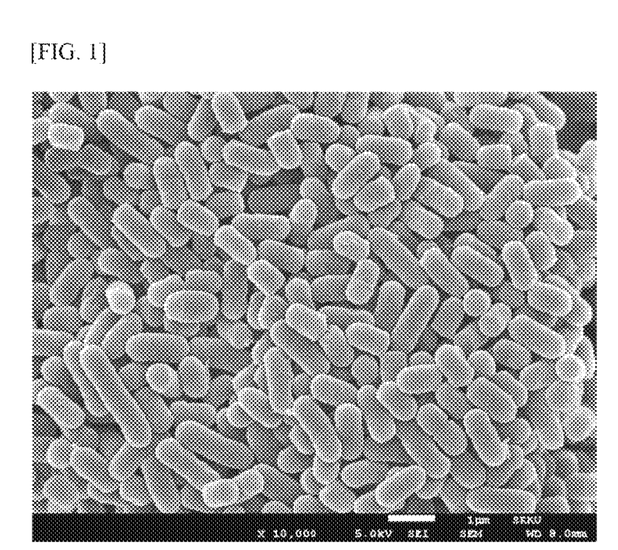
FIG. 1 shows an electron microscope image of CJLP475.

For the identification of the CJLP475 strain, morphological and biochemical characteristics of the strain were primarily investigated. As the morphological characteristics, the strain was gram-positive as a result of Gram staining, and was found to be *bacillus* which was confirmed by electron microscopy (FIG. 1). In order to analyze the biochemical characteristics, the sugar fermentation patterns of the strain were analyzed with the API 50CHL system (biomerieux Vitek, Inc., France) (Table 3).

TABLE 3

| Analysis of Sugar Fermentation Patterns of Isolated Strain | | | |
| --- | --- | --- | --- |
| Name of strain | CJLP475 | Name of strain | CJLP475 |
| Control | − | Esculin | + |
| Glycerol | − | Salicine | + |
| Erythritol | − | Cellobiose | + |
| D-Arabinose | − | Maltose | + |
| L-Arabinose | + | Lactose | + |
| Ribose | + | Melibiose | + |
| D-Xylose | − | Saccharose | + |
| L-Xylose | − | Trehalose | + |
| Adonitol | − | Inulin | − |
| β Methyl-xyloside | − | Melezitose | + |
| Galactose | + | D-Raffinose | + |
| D-Glucose | + | Amidon | − |
| D-Fructose | + | Glycogen | − |
| D-Mannose | + | Xylitol | − |
| L-sorbose | − | β Gentiobiose | + |
| Rhamnose | + | D-Turanose | + |
| Dulcitol | − | D-Lyxose | − |
| Inositol | − | D-Tagatose | − |
| Mannitol | + | D-Fucose | − |
| Sorbitol | + | L-Fucose | − |
| α Methyl-D-mannoside | + | D-Arabitol | − |
| α Methyl-D-glucoside | − | L-Arabitol | − |
| N Acetyl glucosamine | + | Gluconate | + |
| Amygdaline | + | 2 ceto-gluconate | − |
| Arbutin | + | 5 ceto-gluconate | − |

+ : Positive,
− : Negative 1-4. Identification of Strains

In order to more accurately identify the strains, a molecular phylogenetic method based on DNA sequence was performed. Sequence analysis was performed as follows: the gene of 16s rDNA was amplified using PCR premix (Bioneer, Korea) and universal primers 27F (5' AGAGTTTGATCMTGGCTCAG 3', SEQ ID NO: 2) and 1492R (5' GGTTACCTTGTTACGACTT 3', SEQ ID NO: 3). For the amplification of the gene, the total volume of the reaction solution was adjusted to 20 μL, and the reaction was performed at 94° C. for 1 minute, at 56° C. for 1 minute, and at 72° C. for 1 minute, and this cycle was repeated 30 times in total to analyze the amplified DNA sequence. The analyzed 16s rDNA nucleotide sequence of the isolated strain is represented by SEQ ID NO: 1.

As a result of the analysis, CJLP475 was identified as a microorganism having 99% homology with *Lactobacillus plantarum*. Therefore, the isolated strain was named "*Lactobacillus plantarum* CJLP475", and the newly identified microorganism was deposited at the Korean Culture Center of Microorganisms, an International Depositary Authority, under Budapest Treaty on Jul. 11, 2018, with Accession No. KCCM12287P.

Example 2: Assessment of Safety of Strains 2-1. Confirmation of Hemolytic Activity of Strains β-Hemolysis is a phenomenon in which phospholipids supplied by red blood cells are hydrolyzed by phospholipid enzymes produced from harmful bacteria, resulting in hemolysis of red blood cells. In order to determine the hemolytic activity of the *Lactobacillus plantarum* CJLP475 strain, blood agar plates (sheep blood 5% agar, Hanilkomed, Korea) were used. The strain was streaked into the prepared blood agar plates and incubated at 37° C. for 24 hours to confirm the hemolysis.

Figure 2:
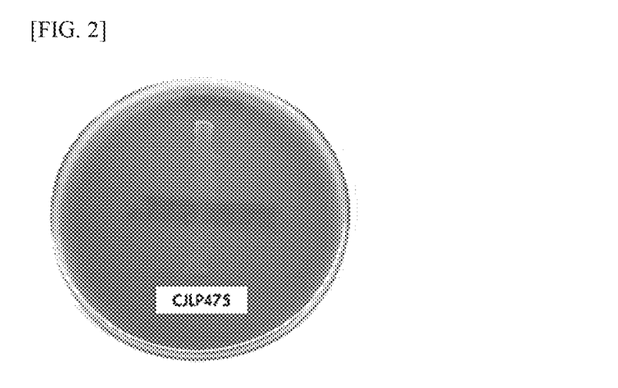
FIG. 2 shows an image of blood agar plate confirming no hemolytic activity of the strain.

As a result, as shown in FIG. 2, it was confirmed that the *Lactobacillus plantarum* CJLP475 strain did not show hemolysis. These results suggest that it does not act as harmful bacteria in vivo.

2-2. Assessment of Antibiotic Susceptibility

The CJLP475 strain was inoculated into a liquid MRS medium and subjected to a static culture at 37° C. for 24 hours. The thus-cultured bacteria were soaked in sterilized cotton swabs and smeared on a solid Mueller Hinton II medium (Difco), and then antibiotic discs were placed on the medium and incubated at 37° C. for 24 hours. Ampicillin, clindamycin, gentamicin, kanamycin, erythromycin, ampicillin/sulbactam, chloramphenicol, and streptomycin discs (Oxoid, UK) were used as antibiotic discs for the antibiotic test.

As a result of the antibiotic susceptibility test of the *Lactobacillus plantarum* CJLP475 strain, the CJLP475 strain was not resistant to the above antibiotics (Table 4). Therefore, it can be found that even if the *Lactobacillus plantarum* CJLP475 strain is used in pharmaceuticals, health functional foods, feed additives, etc., problems that may arise with respect to the resistance and environmental problems are less likely to occur, considering that they have no resistance to antibiotics.

TABLE 4

Inhibition of Bacterial Growth According to Antibiotics

| Antibiotics | Radius of Growth Inhibition Area Centered Around Antibiotics (mm) CJLP475 |
|---|---|
| Amp10 (Ampicillin) | 7 |
| C30 (Clindamycin) | 8 |
| CN120 (Gentamicin) | 9 |
| K30 (Kanamycin) | 1.5 |

TABLE 4-continued

Inhibition of Bacterial Growth According to Antibiotics

| Antibiotics | Radius of Growth Inhibition Area Centered Around Antibiotics (mm) CJLP475 |
|---|---|
| E15 (Erythromycin) | 9 |
| SAM20 (Ampicillin/Sulbactam) | 8 |
| S10 (Chloramphenicol) | 3 |
| DA2 (Streptomycin) | 4 |

Example 3: Assessment of Cytotoxicity

In order to investigate the effect of the strain on the survival of cells, the MTS assay was carried out using (3-(4,5-dimethyl-2-yl)-5-(3-carboxymethoxyphenyl)-2-(4-sulfophenyl)-2H-tetrazolium, (promega, USA) to assess the level of cytotoxicity on IPEC-J2 cells (intestinal pig epithelium cells). Each cell was incubated on a 96-well cell culture plate and treated with the CJLP475 at different concentrations from $10^3$ CFU/mL to $10^8$ CFU/mL for 2 hours. After 24 hours, the MTS solution was added to the cell culture broth, and the cells were incubated for 2 hours, and the cell survival rate (%) was calculated by measuring the absorbance at 490 nm with a microplate reader.

Figure 3:
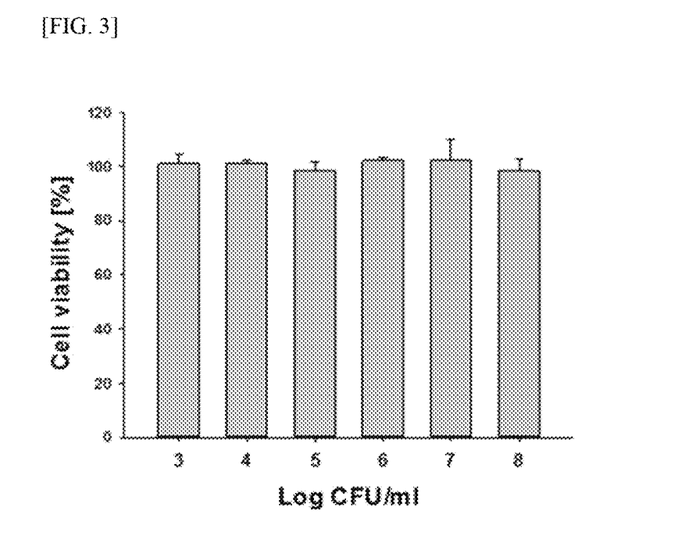
FIG. 3 is a graph confirming no cytotoxicity of the strain.

As a result, as shown in FIG. 3, when the cells were treated at six different concentrations, it was confirmed that cell ($5 \times 10^4$ cells/well) death was hardly observed at concentrations of $10^8$ CFU/mL or below.

Example 4: Assessment of Immune-Enhancing Activity

In order to confirm the immune-enhancing effect of the CJLP475 strain. IPEC-J2 cells were incubated in DMEM/F-12 medium (Dulbecco's Modified Eagle Medium: Nutrient Mixture F-12). In addition, the lymphocytes in mesenteric lymph nodes (mLN), peripheral blood mononuclear cells (PBMC), cells in Peyer's patches, and splenocytes (Spin) were collected from 21-day-old weaned piglets, and immune cells were obtained from each tissue and serum by the following method.

In order to obtain immune cells from the spleen (Spin) and the mesenteric lymph nodes (mLN), the chopped tissue was powdered using a plunger of a syringe and a 70-micrometer cell strainer (BD Falcon), and then the cells were washed using an RPMI-1640 medium (Roswell Park Memorial Institute-1640, Gibco BRL, Grand Island, N.Y., USA). The remaining RBCs (red blood cells) were removed using an RBC lysis buffer (eBioscience, USA) prior to the last washing step. The immune cells collected after the last washing step were stained with Trypan blue and counted with a hemocytometer to be used.

In order to obtain cells in Peyer's patches, the corresponding tissues were isolated from the small intestine, and then chopped and powdered using a surgical scissor. Subsequently, the cells were reacted in RPMI-1640 medium (pH 7.2) containing Dnase I (Roche, Germany), Dispase II (Sigma aldrich, USA), antibiotics, FBS, 15 mM 4-(2-hydroxyethyl)-1-piperazineethanesulfonic acid (HEPES) for 1 hour to obtain single cells. Thereafter, the immune cells were obtained in the same manner as described above.

The collected blood was mixed with PBS at a ratio of 1:1 and centrifuged on a Ficoll-Paque Plus (GE Healthcare Life Sciences, NJ, USA) to separate the WBC (white blood cell)

aggregation layer, and the peripheral blood mononuclear cells were obtained from the separated layer.

In order to evaluate the immune-enhancing effect, the *Lactobacillus plantarum* CJLP475 strain was mixed with each type of immune cells at a ratio of 10:1, and the mixture was incubated at 37° C. in a cell incubator containing 5% $CO_2$ for 20 hours. After completion of the incubation, the cells were centrifuged, and the immune-activating effect of the culture supernatant was evaluated using a cytokine ELISA (Enzyme-linked Immunosorbent Assay). More specifically, the ELISA (R&D Systems, USA) was carried out for IL-12 (interleukin-12), which activates a Th1 (T helper 1)-related immune mechanism that defends against external invasive factors (pathogen), and IL-10 (interleukin-10), which regulates the inflammatory response through Th2 (T helper 2) and indicates acquired immunity.

Figure 4:
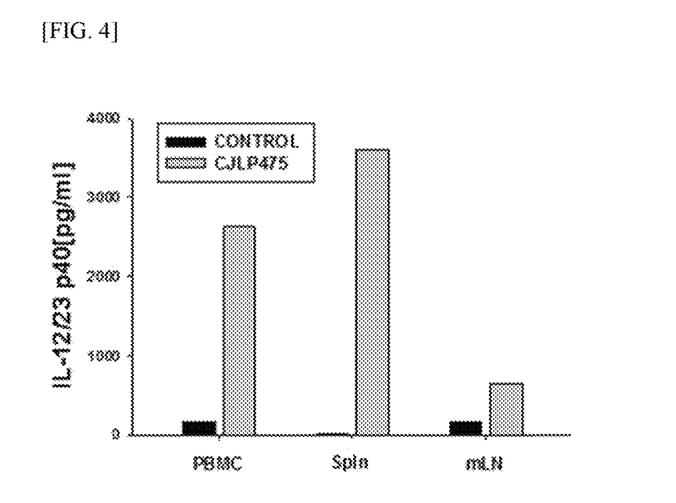
FIG. 4 is a graph showing the measurement results of IL-12 secretion after culturing peripheral blood mononuclear cells (PBMC), splenocytes (Spin), and lymphocytes in mesenteric lymph nodes (mLN) of pigs.
Figure 5:
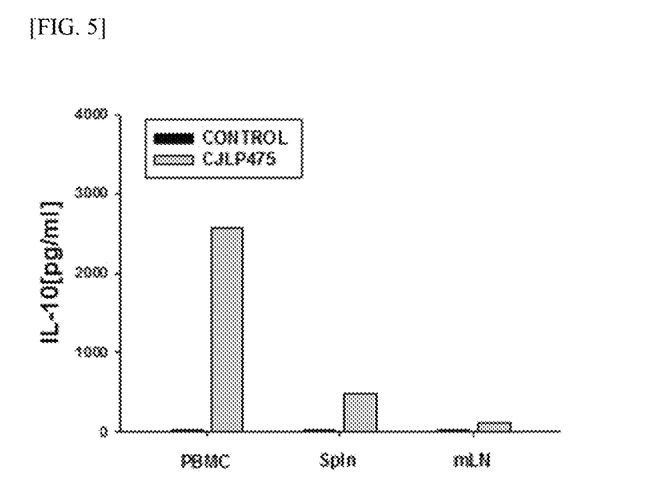
FIG. 5 is a graph showing the measurement results of IL-10 secretion after culturing peripheral blood mononuclear cells (PBMC), splenocytes (Spin), and lymphocytes in mesenteric lymph nodes (mLN) of pigs.

The graphs showing the measurement results for IL-12 and IL-10 are shown in FIGS. 4 and 5, respectively. In each graph, the control was used as a negative control without strain treatment.

As a result, as shown in FIGS. 4 and 5, it was confirmed that the *Lactobacillus plantarum* CJLP475 strain showed the activity of increasing the secretion of IL-12 and IL-10 by stimulating the immune cells. Therefore, it can be seen that the CJLP475 strain exhibits the effect of maintaining the balance of the Th1/Th2 immune responses by simultaneously enhancing the Th1 immune mechanism and the Th2 immune mechanism.

Example 5: Inhibitory Effect Against Viral Infection

In order to measure the inhibitory effect of the CJLP475 strain against viral infection, porcine epidemic diarrhea virus (PEDV, SM98 or KPEDV9 strain) was prepared. Specifically, the virus was proliferated in Vero cells (CCL-81, kidney epithelial cells extracted from Chlorocebus), and MEM (Eagle's Minimum Essential Medium, Gibco BRL, USA), heat-inactivated 10% FBS (fetal bovine serum, v/v) and 1% (v/v) penicillin/streptomycin were as the media for culturing Vero cells. The Vero cells were incubated as a monolayer, washed twice with the media, and then all the solutions were removed. The virus was mixed at 0.1 MOI (multiplicity of infection) level in FBS-free MEM containing trypsin treated with 5 µg/ml TPCK (N-tosyl-L-phenylalanine chloromethyl ketone), treated with a minimal volume of the prepared culture cells, and then incubated in a 37° C. cell incubator containing 5% $CO_2$ for 2 to 3 days.

The viral infection was determined by the formation of virus syncytia. When a virus syncytium was formed, the virus culture broth was collected within 3 to 6 hours, and the cells were removed using a centrifuge and stored at −80° C. For the calculation of the infection titer of the virus, the Vero cells were incubated in a 96-well plate at a density of $2\times10^4$ cells/0.1 mL, and the cells were washed with PBS. Subsequently, the cells were added with a culture broth, in which the virus was subjected to a 2-fold serial dilution, and incubated for 24 to 48 hours to confirm viral infection, and the virus titer was calculated by the Reed & Muench method.

In order to measure the inhibitory effect of the CJLP475 strain against viral infection, the CJLP475 strain and the four types of immune cells extracted in Example 4 were reacted for 20 to 24 hours to obtain a culture broth. Thereafter, the culture broth was independently treated on the 96-well cell culture plate, in which IPEC-J2 was incubated, and incubated in a 37° C. cell incubator containing 5% $CO_2$ for 2 to 4 hours. The PED virus (SM98 or KPEDV9) at a dose of 100 $TCID_{50}$/ml (50% of tissue cell infectious dose) was aliquoted to each plate and incubated for 48 hours. In order to confirm the viral infection, the cell culture plate was fixed with methanol after completion of the culture, stained with crystal violet, and then the wells in which the cells were denatured, were examined with a microscope, thereby confirming the viral infection.

TABLE 5

Inhibitory Effect against PED virus infection (SM98/KPEDV9 strain) of *Lactobacillus plantarum* CJLP475 by Activating Immune Cells

| | mLN | | Peyer's patches | | PBMC | | Spin | |
|---|---|---|---|---|---|---|---|---|
| | SM98 | KPEDV9 | SM98 | KPEDV9 | SM98 | KPEDV9 | SM98 | KPEDV9 |
| Negative Control | − | − | − | − | − | − | − | − |
| CJLP475 | ++ | ++ | + | ++ | ++ | ++ | ++ | ++ |

++: Complete Inhibition,
+: Partial Inhibition,
−: Infected

Figure 6:
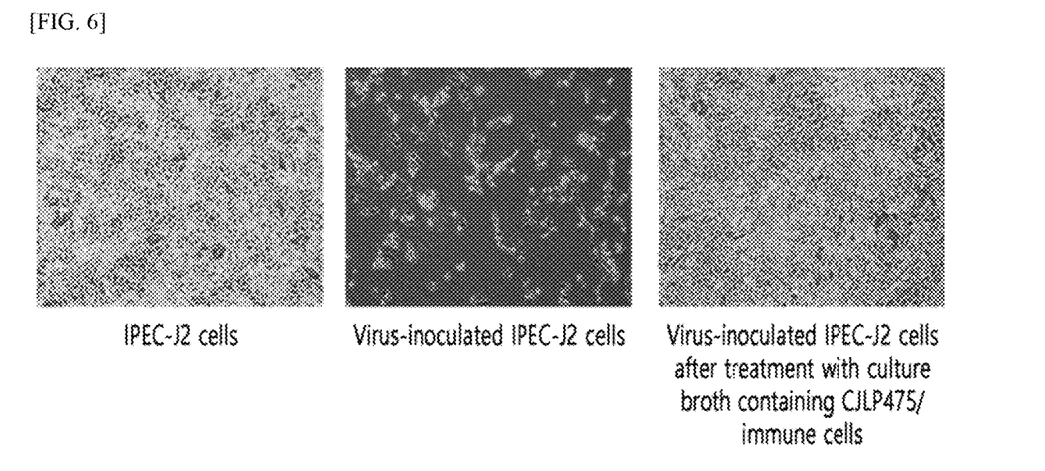
FIG. 6 shows microscopic images illustrating the inhibitory effect against PED virus by the *Lactobacillus plantarum* CJLP475 strain.

As a result, as shown in Table 5 and FIG. 6, it was confirmed that when the immune cells of pigs and the *Lactobacillus plantarum* CJLP475 were treated together, the immune cells were activated by the strain, and the virus infection was remarkably suppressed. Thus, when the immune cells are treated in combination with CJLP475, it shows an excellent antiviral activity against PED virus.

Example 6: Confirmation of Effect on Immunity of Livestock

In order to confirm the effect of the *Lactobacillus plantarum* CJLP475 strain on the immunity of livestock, an experiment was carried out as follows:

Sixteen 21-day-old weaned piglets were purchased and raised in a container farm for 3 weeks. The feed was given in the form of common crumble feeds without antibiotics. The *Lactobacillus plantarum* CJLP475 strain was produced in the form of freeze-dried powder and stored in a refrigerator, and thoroughly mixed to the crumble feeds for oral administration such that each piglet could ingest the feed in an amount of $10^{10}$ CFU per day. After 3 weeks of oral administration, four piglets per treatment group were autopsied to collect blood and tissue samples so as to determine the effect of the strain on the immunity of the piglets. For evaluation of the immune-enhancing activity, immune cells were obtained from the spleen and cultured, and the ELISA test was performed in the same manner as described in Example 5.

Meanwhile, the immune cells obtained from the weaned piglets without feeding the strains were used for a control group. Specifically, the immune-enhancing activity of the culture supernatant, in which the immune cells obtained from the weaned piglets fed without the CJLP475 strain were cultured, was evaluated.

Figure 7:
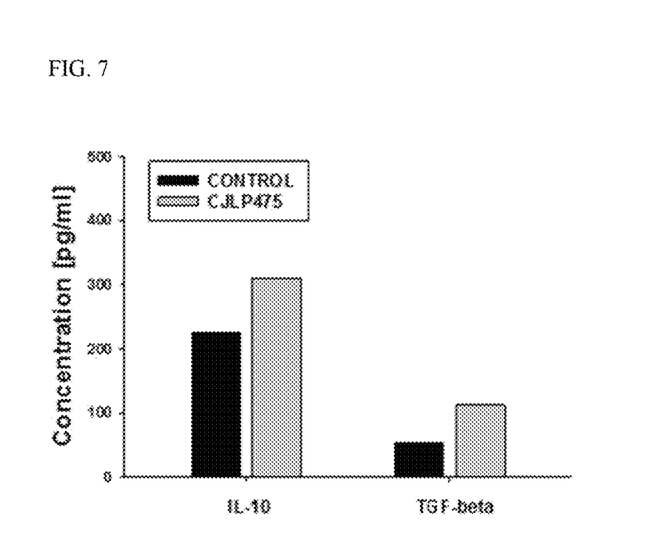
FIG. 7 is a graph showing the measurement results of IL-10 and TGF-beta secretion after oral administration of the CJLP475, followed by isolation of splenocytes in weaned pigs.
Figure 8A:
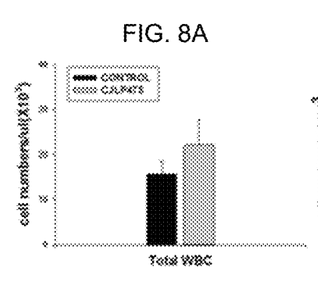
FIGS. 8A-8C shows the graphs analyzing the total number of WBC, lymphocytes, and monocytes in the serum of weaned pigs after oral administration of the CJLP475 strain.
Figure 8B:
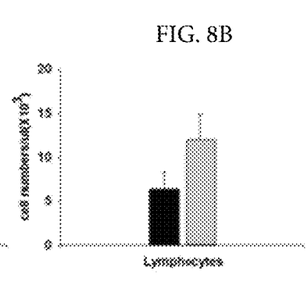
Figure 8C:
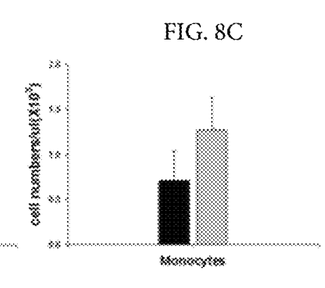

FIG. 7 is a graph showing the measurement results of IL-10 and TGF-beta. In addition, FIGS. 8A-8C show the results of serum analysis.

As a result, as shown in FIG. 7, it was confirmed that secretion of IL-10 and TGF-beta was increased in the splenocytes of the weaned pigs fed with the feed containing the CJLP475. Thus, it can be seen that CJLP475 enhances the Th2 immune mechanism and thereby exhibits an anti-inflammatory effect. In addition, as shown in FIGS. 8A-8C, it was confirmed that total WBC (white blood cells) was increased in the serum of the weaned piglets fed with the feed containing CJLP475. Among them, it can be found that the CJLP475 exhibits an immune-activating effect through the increase in the number of lymphocytes (T cells and B cells) and monocytes.

Example 7: Preparation of Probiotics Including *Lactobacillus plantarum* CJLP475 Strain The probiotic *Lactobacillus plantarum* CJLP475 strain identified in Example 1 was produced on a mass-scale and freeze-dried to make probiotics suitable for use as a raw material of pharmaceuticals, foods, feeds, feed additives or cosmetics.

For production of the strain, the strain was incubated in a liquid MRS medium (Difco) at 37° C. for 18 hours while adjusting the pH to 6.0 with a 25% NaOH solution, followed by harvesting the cells by centrifugation. The recovered cells were frozen at −40° C. with 5% dextrin and 10% skim milk serving as cryoprotectants, dried at 37° C. and powdered using a mixer. The number of bacteria was adjusted to a desired level. Then, the bacteria were mixed with a suitable amount of an excipient such as glucose, lactose and skim milk, and packaged in a sealable aluminum pouch.

The probiotics can be applied to various fields in accordance with a conventional method in the art, such as pharmaceuticals, foods, feeds, cosmetics and the like. For example, the prepared probiotics may be mixed with grain powder used as a raw material for feeds to be used as probiotics for feeds, may be mixed with an excipient or additive to be used as probiotics for pharmaceuticals in the form of tablets, capsules and for foods, or may be mixed in a predetermined amount with raw materials of cosmetics to be used as probiotics for cosmetics.

While the present disclosure has been described with reference to the particular illustrative embodiments, it will be understood by those skilled in the art to which the present disclosure pertains that the present disclosure may be embodied in other specific forms without departing from the technical spirit or essential characteristics of the present disclosure. Therefore, the embodiments described above are considered to be illustrative in all respects and not restrictive. Furthermore, the scope of the present disclosure is defined by the appended claims rather than the detailed description, and it should be understood that all modifications or variations derived from the meanings and scope of the present disclosure and equivalents thereof are included in the scope of the appended claims

The invention claimed is:

1. A composition comprising (i) the isolated *Lactobacillus plantarum* CJLP475 strain deposited under Accession No. KCCM12287P, a lysate thereof, a culture thereof, a concentrate thereof, or a dried form thereof, and (ii) a cryoprotectant.

2. The composition of claim 1, wherein the cryoprotectant is at least one selected from the group consisting of glycerol, trehalose, maltodextrin, skim milk powder and starch.

3. The composition of claim 1, wherein the composition comprises a freeze-dried form of the *Lactobacillus plantarum* CJLP475 strain, and wherein the *Lactobacillus plantarum* CJLP475 strain is in a live state.

4. A method of enhancing immunity of a mammalian subject, the method comprising administering the composition according to claim 1 to the subject.

5. A composition comprising (i) the isolated *Lactobacillus plantarum* CJLP475 strain deposited under Accession No. KCCM12287P, a lysate thereof, a culture thereof, a concentrate thereof, or a dried form thereof, and (ii) an amount of a cryoprotectant, wherein the composition is a freeze-dried composition.

6. The composition of claim 1, wherein the composition is a probiotic composition, a food composition, or a feed composition.

* * * * *